United States Patent [19]
Bek

[11] Patent Number: 5,628,745
[45] Date of Patent: May 13, 1997

[54] EXIT SPARK CONTROL FOR AN ELECTROSURGICAL GENERATOR

[76] Inventor: Robin B. Bek, 4524 Starboard Ct., Boulder, Colo. 80301

[21] Appl. No.: 479,424

[22] Filed: Jun. 6, 1995

[51] Int. Cl.$^6$ .................................................. A61B 17/39
[52] U.S. Cl. ............................... 606/38; 606/39; 606/40
[58] Field of Search ........................................ 606/37–40

[56] References Cited

U.S. PATENT DOCUMENTS

| | | |
|---|---|---|
| 3,964,487 | 6/1976 | Judson . |
| 3,980,085 | 9/1976 | Ikuno . |
| 4,092,986 | 6/1978 | Schneiderman . |
| 4,094,320 | 6/1978 | Newton et al. . |
| 4,114,623 | 9/1978 | Meinke et al. ............................ 606/38 |
| 4,188,927 | 2/1980 | Harris . |
| 4,321,926 | 3/1982 | Roge . |
| 4,372,315 | 2/1983 | Shapiro et al. . |
| 4,658,819 | 4/1987 | Harris et al. . |
| 4,969,885 | 11/1990 | Farin . |
| 5,133,711 | 7/1992 | Hagen ...................................... 606/38 |

Primary Examiner—Lee S. Cohen
Attorney, Agent, or Firm—Peter C. Richardson; Lawrence C. Akers; Aaron Passman

[57] ABSTRACT

An electrosurgical generator is disclosed that includes an exit spark control system. Exit sparking occurs when energy arcs to the patient as the active electrode is withdrawn from the patient. A basis for controlling the exit spark is to automatically change the frequency at which the final amplifier is driven whenever the conditions for an exit spark are detected. The change in frequency acts to lower the gain and efficiency in the final amplifier and dissipate energy as heat. The exit spark control system includes a frequency adjustable waveform generator and a logic capability for determining the conditions when exit sparking is likely to occur. Sensors and an algorithm in a microcontroller are preferably required to detect the conditions preceding exit sparking occurrence. It is further preferred that, the algorithm also control the sequencing of events: first stopping the electrosurgical output to prevent an arc from initiating and then changing the driving frequency appropriately to dissipate excess stored energy. The output waveform may be stopped for only a short time or the surgeon will detect drag while cutting through tissue.

8 Claims, 2 Drawing Sheets

EXIT SPARK CONTROL FOR AN ELECTROSURGICAL GENERATOR

Related applications incorporated herein and made a part hereof by reference and filed on the same date as this application:

Power Control for an Electrosurgical Generator; U.S. Ser. No. 08/471,116; PC8826;

Digital Waveform Generation for Electrosurgical Generators; U.S. Ser. No. 08/471,344; PC9210;

A Control System for Neurosurgery; U.S. Ser. No. 08/470,533; PC9162;

Control Apparatus for Electrosurgical Generator Power Output; U.S. Ser. No. 08/468,950; PC8827.

FIELD OF THE INVENTION

This invention pertains to electrosurgical generators, and more particularly to a design for electrosurgical generators that diminishes the severity of exit sparking when the electrode is removed from the tissue.

BACKGROUND OF THE DISCLOSURE

An electrosurgical generator is used in surgical procedures to deliver electrical power to the tissue of a patient. An electrosurgical generator includes a radio frequency generator and its controls. When an electrode is connected to the generator, the electrode can be used for cutting or coagulating the tissue of a patient with the high frequency electrical energy. During operation, current flows from the generator through an active electrode, through the tissue and bodily fluids of a patient, and back to the generator through a return electrode. The electrical circuit formed by the electrodes and the patient is referred to as the patient circuit.

The electrical energy has its waveform shaped to enhance its ability to cut or coagulate tissue. Different waveforms correspond to different modes of operation of the generator, and each mode gives the surgeon various operating advantages. Modes may include cut, coagulate, a blend thereof desiccate or spray.

One problem that may be encountered in the use of electrosurgical equipment is that the electrode will arc to the patient as the electrode is withdrawn from the tissue. This is due to power control systems in the electrosurgical generator which are designed to increase the output voltage as higher impedances are presented by the tissue. This is usually done to maintain the output power. In the case of withdrawal of the electrode, the control system in the electrosurgical generator may function as though the tissue impedance has increased dramatically and try to maintain power delivery. The control system may rapidly increase the voltage, thus causing the active electrode to arc to the tissue as it is withdrawn, This phenomenon is called "exit sparking," and it is undesirable because it causes unwanted tissue damage. Designers of electrosurgical generators want to minimize this outcome.

Exit sparking may also occur because electrical energy is stored in the capacitive and inductive elements of the final amplifier stage in an electrosurgical generator. Even though the generator output can be turned off once the electrode is removed from the tissue, the energy that is stored in the final amplifier stage must be dissipated. If no other dissipation path is available, the stored energy might arc to the patient.

Early designs for electrosurgical generators avoided the problems of exit sparking is several ways. One way to avoid exit sparking is to prevent high voltages from occurring at the active electrode. High voltages can be prevented by actively controlling the output voltage or else by passive means. In many early generators, the electrical capabilities of the generator where not sufficient to produce high voltages at the active electrode when the impedance of the load was high, and therefore the problem of exit sparking was passively avoided.

Closed loop power control systems in modern electrosurgical generators may enhance the possibility of exit sparking. Closed loop control of output power could cause the output voltage of the generator to rise as the impedance of the tissue is increased. As the active electrode is withdrawn from the tissue, the measured impedance of the load can rise sharply. The closed loop control system increases the voltage in response to this perceived rise in impedance. The resulting high output voltage could cause an exit spark.

U.S. Pat. No. 4,969,885 discloses an active control apparatus for controlling the output voltage of an electrosurgical generator. Since exit sparking is most likely a problem in generators that control output power (rather than output voltage), the '885 patent does not contemplate the problem of exit sparking.

U.S. Pat. No. 5,099,840 discloses an electrosurgical generator that adjusts the resonant frequency of its output stage in accordance with the impedance of the load. This is done to increase the efficiency of the output stage. The problem of exit sparking is not contemplated in the '840 patent. In contrast to the '840 patent, the present invention seeks to decrease the gain, and hence decrease the efficiency of the output stage in order to avoid exit sparking. This is the opposite result of the '840 patent.

Other U.S. Patents have related technology, but none are directed at the problem of exit spark control. U.S. Pat. No. 4,658,819 has a circuit wherein the power delivered to the electrode is a function of the voltage from a DC supply and the load as measured by sensors of load voltage and current. A microprocessor controller digitizes the sensing signals and computes the load impedance and actual power being delivered. The microprocessor controller accordingly repeats the measurement, calculation and correction process approximately as long as the generator is operating. U.S. Pat. No. 4,372,315 discloses a circuit which measures impedances after delivering a set number of radio frequency pulses on a pulse burst by pulse burst basis. U.S. Pat. No. 4,321,926 has a feedback system to control electrosurgical effect delivery but the impedance sensing is not on a real time basis. U.S. Pat. Nos. 3,964,487, 3,980,085, 4,188,927, and 4,092,986 have circuitry to reduce the output current in accordance with increasing load impedance. In those patents voltage output is maintained constant while the current is decreased with increasing load impedance. U.S. Pat. No. 4,094,320 has a circuit that responds to impedance changes as measured by sensing current in the active and return leads. The sensed currents are subtracted from one another and if that exceeds a variable threshold the generator is turned off. The variable threshold is a function of power level and leakage current through stray capacitance.

One of the purposes of the present invention is to overcome the problem of exit sparking while still allowing for high power at the active electrode.

SUMMARY OF THE INVENTION

An electrosurgical generator is disclosed that includes an exit spark control system. A basis for controlling the exit spark is to make temporary adjustments to the operation of the electrosurgical generator whenever conditions are likely for an exit spark to occur. The adjustments include momentarily shutting off the output of the electrosurgical generator and then temporarily changing the driving frequency of the output stage of the electrosurgical generator in order to reduce the gain of the output stage.

Amplifier circuits are tuned to operate efficiently at a particular frequency. Driving the amplifier circuit at a different frequency results in a "detuned" condition that presents a lower gain and efficiency. However, a detuned condition will stress the electrical components and therefore should be performed only for brief periods of time.

Sensors and an algorithm in a microcontroller are preferably required to detect the conditions preceding exit sparking occurrence. It is further preferred that, the algorithm also control the sequencing of events: first stopping the electrosurgical output to prevent an arc from initiating and then changing the driving frequency appropriately to dissipate excess stored energy. The output waveform may be stopped for only a short time or the surgeon will detect drag while cutting through tissue. Preferably, this time is between five and two hundred milliseconds.

Two events that signal the condition for an exit spark to occur have been recognized. A first event is that the electrosurgical generator has been activated to treat tissue of a patient and is in fact treating tissue. This is needed because the spark for initiation of electrosurgery must not be influenced by the exit spark control. This first event can be sensed by an impedance monitoring function of the electrosurgical generator. Preferably whenever the impedance is in a typical operating range, for example, below 4096 ohms, it is believed that the active electrode is in the tissue of the patient.

A second event is when the comparator puts out a high signal indicating that the output voltage has crossed the voltage threshold. Another way of sensing the conditions for exit spark control would be to monitor the impedance of the load. In a closed-loop power control system, the output voltage would increase with increasing impedance.

Typically the voltage threshold would be set at 80% of the peak voltage expected for the ordinary operating conditions. Since the electrosurgical generator has many operating conditions with different peak voltages, a microprocessor stores, maintains, and sets suitable voltage thresholds for each such operating condition. Typically, these thresholds will depend primarily on the power setting that the surgeon has selected, and on the mode of operation, i.e. cut, blend or desiccate. For example, low power settings in the cut mode results in a low voltage threshold. However, the voltage threshold could also be a constant value that is high enough to induce an exit spark.

In some modes of operation, exit sparking may not present a problem for surgeons. Typically these modes would be coagulation modes, such as fulgurate or spray. In each of these modes, sparks are expected to emanate from the active electrode, and therefore exit spark control might be used only to limit the peak voltage at which the sparks are delivered.

The exit spark control system usually involves a combination of hardware and software in the electrosurgical generator. The software can be arranged to execute logical steps for determining the conditions for exit sparking occurrence. In some electrosurgical generators, the waveforms are preferably produced by microprocessors and therefore in those some additional software may be required to change the frequency of the waveforms in response to a signal that exit sparking might occur. Hardware circuits may be used to check the behavior of the output of the voltage sensor.

DETAILED DESCRIPTION OF THE INVENTION

Figure 1:
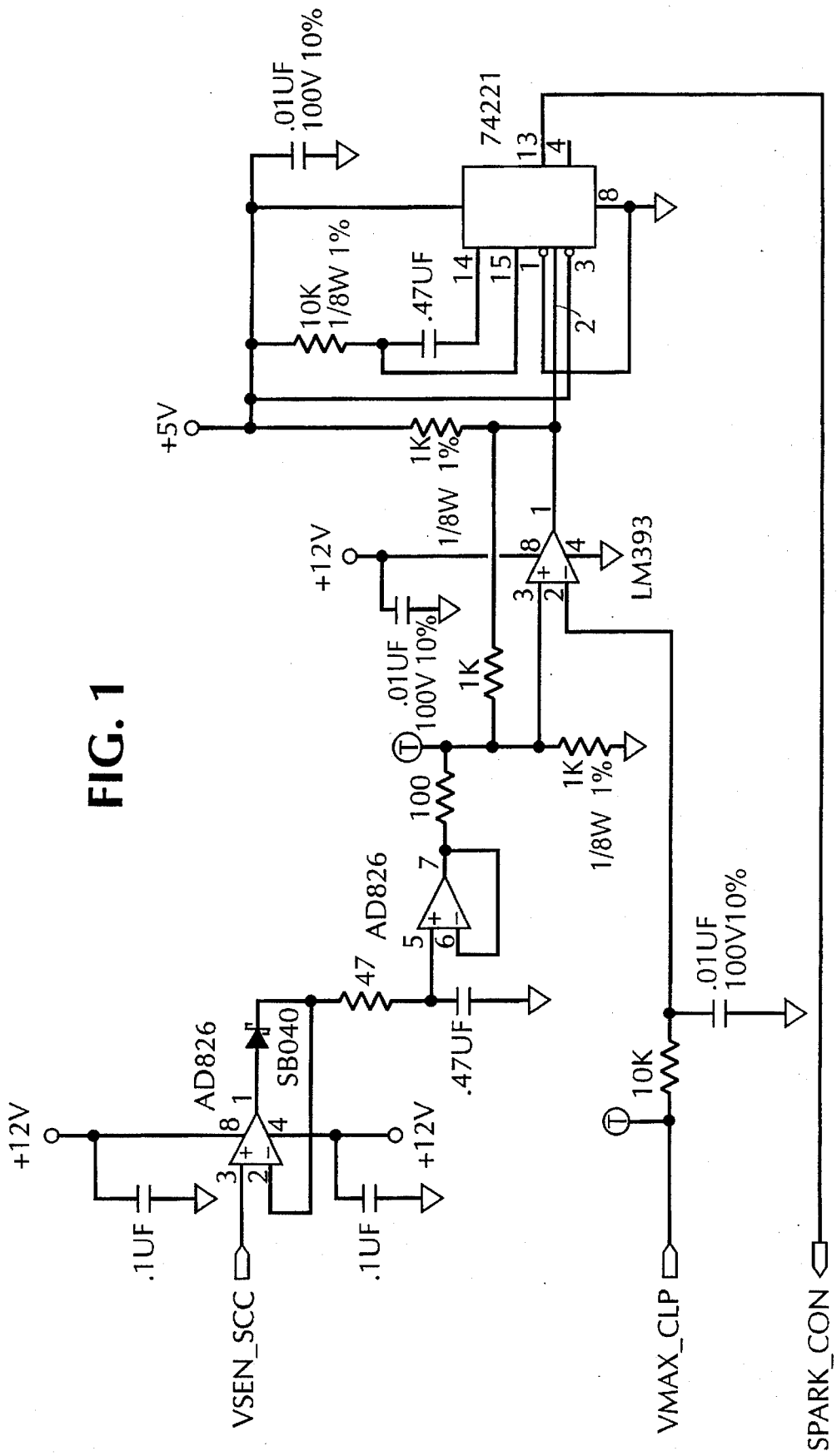
FIG.1 is a schematic circuit diagram of a spark control circuit.
Figure 2:
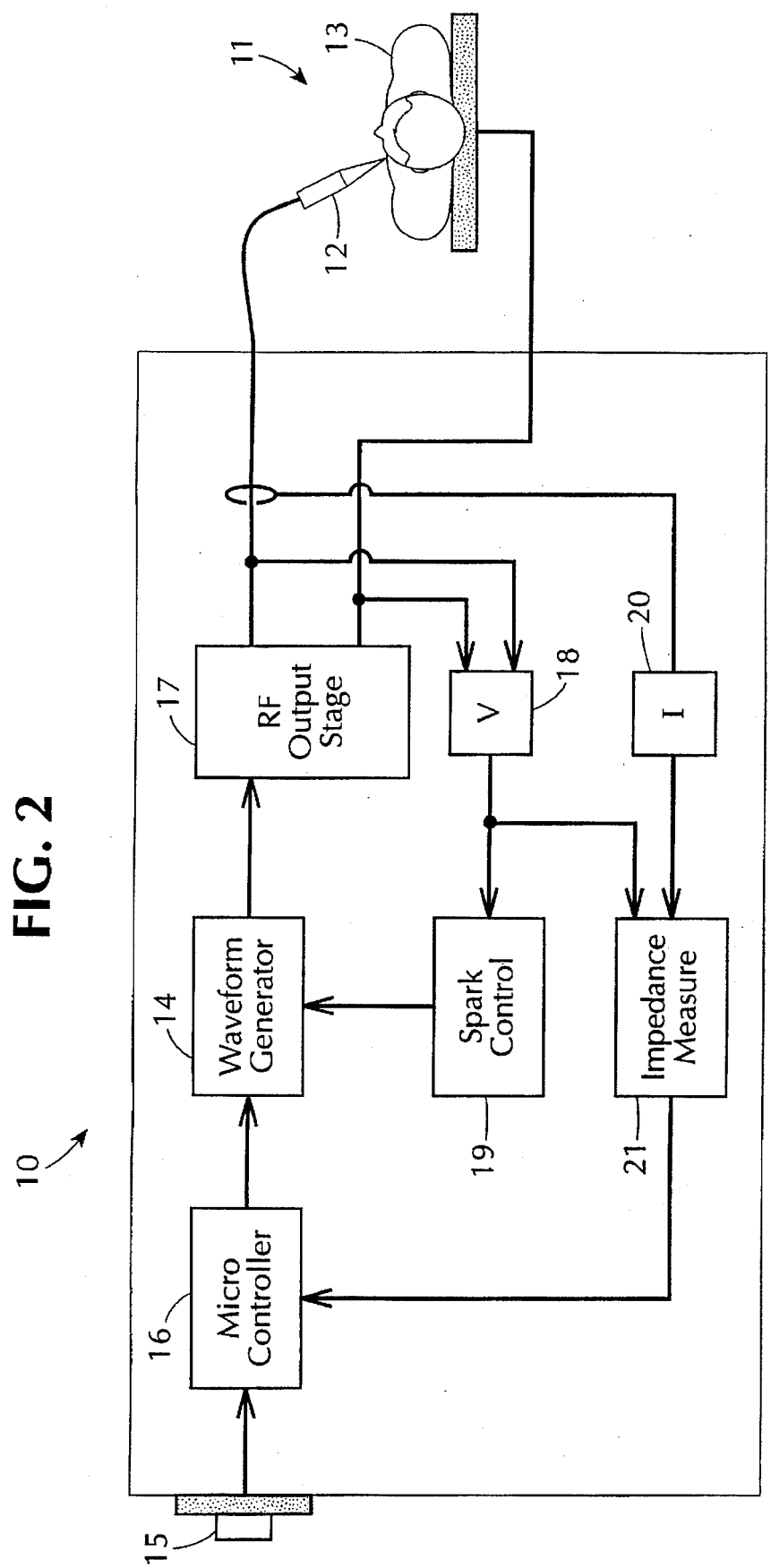
FIG.2 is a functional block diagram of an electrosurgical generator with a spark control system.

An electrosurgical generator 10 has an exit spark control system that suppresses sparking in a patient circuit 11 from the active electrode 12 to the patient 13. The exit spark control system has sensory and logic capability for detecting the conditions when exit sparking is likely to occur, and a waveform generator 14 that is capable of changing its frequency when those conditions have been detected.

The electrosurgical generator 10 has a surgeon panel 15 which is accessible to the surgeon for setting a desired level of output power. The electrosurgical generator 10 also has a microcontroller 16 which is electrically connected to receive the desired level of output power from the surgeon panel 15. The microcontroller 16 is also capable of setting a voltage threshold based on the desired level of output power.

An adjustable waveform generator 14 in the electrosurgical generator 10 is used for producing radio frequency waveforms, and for adjusting the frequency of the waveforms. The adjustable waveform generator 14 may be designed to produce either a digital or analog output. A radio frequency output stage 17 is electrically connected to the adjustable waveform generator 14 for receiving the radio frequency waveforms. The output stage 17 is designed for generating an output voltage and an output current for transmission to the patient circuit 11. A voltage sensor 18 is connected to the radio frequency output stage 17 for receiving the output voltage, and is capable of producing a first signal that is proportional to the output voltage.

A spark control circuit 19 is electrically connected to the microcontroller 16 for receiving the voltage threshold therefrom. The spark control circuit 19 is also electrically connected to the voltage sensor 18 for receiving the first signal, and the spark control circuit 19 is electrically connected to the adjustable waveform generator 14 to temporarily stop and then adjust the frequency of the waveforms. The spark control circuit 19 performs the temporary stop and adjustment partly in response to when the first signal is greater than the voltage threshold. The adjusted frequency causes a drop in gain and efficiency across the radio frequency output stage 17, thus preventing a high voltage from occurring and dissipating energy as heat.

The preferred embodiment of the spark control system comprises a spark control circuit 19 and a microcontroller 16. Referring to FIG. 1, the spark control circuit 19 has a peak detector, a comparator, and a one-shot. The peak detector is connected to the output of the voltage sensor 18. The peak detector is designed to store each local maximum from the output voltage sensor 18. The signal from the output voltage sensor 18 is rectified, but is unfiltered when it reaches the peak detector.

The comparator is connected to receive the peak values from the peak detector and also connected to receive the voltage threshold, which is labeled VMAX_CLP in FIG. 1. The comparator is designed to generate a high signal whenever the peak value exceeds the voltage threshold.

The one-shot is connected to receive the high signal from the comparator. The purpose of the one-shot is to produce a pulse for the microcontroller 16 whenever the comparator generates a high signal. The pulse is labeled SPARK_CON in FIG. 1. The microcontroller 16 has an input for the pulse from the one-shot.

In the preferred embodiment, a spark control circuit 19 is used to test the output of the voltage sensor 18. The rectified but unfiltered waveform from the output voltage sensor 18 is fed into a peak detector having U17A and CR11. This input signal is labeled VSEN_SCC in FIG. 1. U17B is a high impedance buffer to maintain the integrity of the peak detected signal. The output of this buffer is divided down and fed to a comparator having U16A. The other input to the comparator is a threshold level set in the microcontroller 16 which depends on the mode and power setting. When the peak detected sample of the output voltage exceeds the threshold, one-shot U15A is fired and generates a three msec pulse that is sent to the microcontroller 16 board. This pulse is ignored if it occurs during the first approximately 0.2 seconds of activation. Otherwise, the pulse causes the microcontroller 16 to shut off the output from the waveform generator 14 for a period which is between 5 milliseconds and 200 milliseconds in the preferred embodiment.

The microcontroller 16 senses that a spark has been suppressed. In one embodiment, the microcontroller 16 adjusted the shut off time depending on the mode. For example, in desiccate mode the shut off time could be 10 msec, or 100 msec in pure cut mode. The microcontroller 16 then reinitiates the waveform generator 14 at a frequency of 470 kHz. The frequency of the waveform generator 14 returns to 394 kHz. either after one second of continuous activation, or when the generator 10 is reactivated.

In the preferred embodiment, the microcontroller 16 also monitors the impedance of the load on the patient circuit 11 in order to determine one of the conditions precedent to exit sparking. Thus, in the preferred embodiment, the spark control circuit 19 further comprises a current sensor 20 and an impedance measuring device 21. The current sensor 20 is connected to the radio frequency output stage 17 for receiving the output current, and is capable of producing a second signal that is proportional to the output current. The impedance measuring device 21 may be an analog circuit, or a logic device, or else a microprocessor-based device. The impedance measuring device 21 is electrically connected for receiving the first signal and the second signal and for computing the impedance of the load in the patient circuit 11.

In the preferred embodiment, the impedance is subsequently used in the microcontroller 16 for determining the occurrence of events which will enable exit spark control. Once spark control has been enabled, the microcontroller 16 has an algorithm for shutting off the output stage 17 for about 5 milliseconds to 200 milliseconds and thereafter signalling the adjustable waveform generator 14 to adjust the frequency of the waveforms.

A method of controlling exit spark in an electrosurgical generator 10 includes the step of changing the frequency of the adjustable waveform generator 14 whenever conditions for exit sparking are present, so that the gain of the output stage 17 is lowered. In the preferred embodiment, the method further comprises the steps of monitoring the impedance of the output load, monitoring the output voltage, setting a ,voltage threshold, and triggering the spark control system whenever the impedance is less than about 4096 ohms and the voltage is higher than the voltage threshold.

Other steps in a method for controlling exit sparking comprise: setting a desired level of output power on a surgeon panel 15; receiving the desired level of output power from the surgeon panel 15 with a microcontroller 16; setting a voltage threshold based on the desired level of output power with the microcontroller 16; producing radio frequency waveforms with an adjustable waveform generator 14; adjusting the frequency of the waveforms with the adjustable waveform generator 14; receiving the radio frequency waveforms with a radio frequency output stage 17 electrically connected to the adjustable waveform generator 14; generating an output voltage and an output current for transmission to the patient circuit 11 with the radio frequency output stage 17; receiving the output voltage with a voltage sensor 18 connected to the radio frequency output stage 17; producing a first signal that is proportional to the output voltage with the voltage sensor 18; receiving the output current with a current sensor 20 connected to the radio frequency output stage 17; producing a second signal that is proportional to the output current with the current sensor 20; receiving the first signal and the second signal with an impedance measuring circuit electrically connected to the voltage and current sensor 20; computing the impedance of the load in the patient circuit 11 with the impedance measuring circuit; receiving the voltage threshold from the microcontroller 16 with a spark control circuit 19 electrically; receiving the first signal from the voltage sensor 18 with the spark control circuit 19; and adjusting the frequency of the waveforms in response to a condition when the impedance of the load is generally less than about 4096 ohms and the first signal is greater than the voltage threshold.

What is claimed is:

1. An electrosurgical generator with an exit spark control system that suppresses exit sparking in a patient circuit, the electrosurgical generator comprising:

an adjustable waveform generator in the electrosurgical generator for producing radio frequency waveforms, and capable of adjusting the frequency of the waveforms;

a radio frequency output stage electrically connected to the adjustable waveform generator for receiving the radio frequency waveforms and for generating an output voltage and an output current for transmission to the patient circuit;

a voltage sensor connected to the radio frequency output stage for receiving the output voltage, and capable of producing a first signal that is proportional to the output voltage;

a spark control circuit electrically connected to the voltage sensor for receiving the first signal, and the spark control circuit electrically connected to the adjustable waveform generator to cause the waveform generator to temporarily stop and then to temporarily adjust the frequency of the waveforms partly in response to the first signal, wherein the adjusted frequency causes a drop in gain across the radio frequency output stage.

2. The apparatus of claim 1 wherein the spark control circuit further comprises:

a current sensor connected to the radio frequency output stage for receiving the output current, and capable of producing a second signal that is proportional to the output current, and an impedance measuring device electrically connected for receiving the first signal and the second signal and for computing the impedance of the load in the patient circuit.

3. The apparatus of claim 2 further comprising a microcontroller which has an input electrically connected to receive the impedance of the load from the impedance measuring device, and the microcontroller has an output electrically connected to the adjustable waveform generator for enabling the spark control circuit.

4. The apparatus of claim 3 further comprising an algorithm in the microcontroller for shutting off the output stage for a time in the range of 5 milliseconds to 200 milliseconds.

5. The apparatus of claim 1 wherein the spark control circuit further comprises:
- a peak detector which is connected to receive the first signal from the voltage sensor and for holding peak values from the first signal, and
- a comparator which is connected to receive the peak values from the peak detector and also connected to receive a voltage threshold, the comparator generating a high signal whenever the peak value exceeds the voltage threshold;
- a one-shot connected to receive the high signal from the comparator, the one-shot having an output electrically connected to the adjustable waveform generator, the one-shot set to produce a pulse in the output whenever the high signal is received from the comparator.

6. An electrosurgical generator with an exit spark control system that suppresses exit sparking through a patient circuit and to the patient when used by a surgeon, the electrosurgical generator comprising:
- a surgeon panel on the electrosurgical generator which is accessible to the surgeon for setting a desired level of output power;
- a microcontroller in the electrosurgical generator which is electrically connected to receive the desired level of output power from the surgeon panel, and capable of setting a voltage threshold based on the desired level of output power;
- an adjustable waveform generator in the electrosurgical generator for producing radio frequency waveforms, and for adjusting the frequency of the waveforms;
- a radio frequency output stage electrically connected to the adjustable waveform generator for receiving the radio frequency waveforms and for generating an output voltage and an output current for transmission to the patient circuit;
- a voltage sensor connected to the radio frequency output stage for receiving the output voltage, and capable of producing a first signal that is proportional to the output voltage;
- a spark control circuit electrically connected to the microcontroller for receiving the voltage threshold therefrom, and the spark control circuit electrically connected to the voltage sensor for receiving the first signal, and the spark control circuit electrically connected to the adjustable waveform generator to temporarily stop and then adjust the frequency of the waveforms partly in response to when the first signal is greater than the voltage threshold, wherein the adjusted frequency causes a drop in gain and efficiency across the radio frequency output stage.

7. An electrosurgical generator with an exit spark control system that suppresses exit sparking through a patient circuit and to the patient when used by a surgeon, the electrosurgical generator comprising:
- a surgeon panel on the electrosurgical generator which is accessible to the surgeon for setting a desired level of output power;
- a microcontroller in the electrosurgical generator which is electrically connected to receive the desired level of output power from the surgeon panel, and capable of setting a voltage threshold based on the desired level of output power;
- an adjustable waveform generator in the electrosurgical generator for producing radio frequency waveforms, and for adjusting the frequency of the waveforms;
- a radio frequency output stage electrically connected to the adjustable waveform generator for receiving the radio frequency waveforms for generating an output voltage and an output current for transmission to the patient circuit;
- a voltage sensor connected to the radio frequency output stage for receiving the output voltage, and capable of producing a first signal that is proportional to the output voltage;
- a current sensor connected to the radio frequency output stage of receiving the output current, and capable of producing a second signal that is proportional to the output current;
- an impedance measuring circuit electrically connected for receiving the first signal and the second signal and for computing the impedance of the load in the patient circuit;
- a spark control circuit electrically connected to the microcontroller for receiving the voltage threshold therefrom, and the spark control circuit electrically connected to the voltage sensor for receiving the first signal, and the spark control circuit electrically connected to the adjustable waveform generator to adjust the frequency of the waveforms in response to a condition when the impedance of the load is generally less than about 4096 ohms and the first signal is greater than the voltage threshold, wherein the adjusted frequency causes a drop in gain across the radio frequency output stage;
- a peak detector in the spark control circuit which is connected to receive the first signal from the voltage sensor and for holding peak values from the first signal;
- a comparator in the spark control circuit which is connected to receive the peak values from the peak detector and also connected to receive the voltage threshold from the microcontroller, the comparator generating a high signal whenever the peak value exceeds the voltage threshold; and
- a one-shot in the spark control circuit, the one-shot connected to receive the high signal from the comparator, the one-shot having an output electrically connected to the adjustable waveform generator, the one-shot set to produce a pulse in the output whenever the high signal is received from the comparator.

8. A method of controlling exit spark in an electrosurgical generator with an exit spark control system that suppresses exit sparking through a patient circuit and to the patient when used by a surgeon, the method of suppressing including the steps of:
- setting a desired level of output power on a surgeon panel accessible to the surgeon and located on the electrosurgical generator;
- receiving the desired level of output power from the surgeon panel with a microcontroller electrically connected to the electrosurgical generator;
- setting a voltage threshold based on the desired level of output power with the microcontroller;
- producing radio frequency waveforms with an adjustable waveform generator in the electrosurgical generator;

receiving the radio frequency waveforms with a radio frequency output stage electrically connected to the adjustable waveform generator;

generating an output voltage and an output current for transmission to the patient circuit with the radio frequency output stage;

receiving the output voltage with a voltage sensor connected to the radio frequency output stage;

producing a first signal that is proportional to the output voltage with the voltage sensor;

receiving the output current with a current sensor connected to the radio frequency output stage;

producing a second signal that is proportional to the output current with the current sensor;

receiving the first signal and the second signal with an impedance measuring circuit electrically connected to the voltage and current sensors;

computing the impedance of the load in the patient circuit with the impedance measuring circuit;

receiving the voltage threshold from the microcontroller with a spark control circuit electrically;

receiving the first signal from the voltage sensor with the spark control circuit;

adjusting the frequency of the waveforms with the adjustable waveform generator, at least partly in response to the spark control circuit, such that the gain across the output stage is reduced, the adjustment in response to a condition wherein the impedance of the load is generally less than about 4096 ohms and the first signal is greater than the voltage threshold.

* * * * *